United States Patent [19]

Brantigan

[11] Patent Number: 4,878,915
[45] Date of Patent: Nov. 7, 1989

[54] SURGICAL PROSTHETIC IMPLANT FACILITATING VERTEBRAL INTERBODY FUSION

[76] Inventor: John W. Brantigan, 2108 Bramblewood La., Fremont, Nebr. 68025

[21] Appl. No.: 293,578

[22] Filed: Jan. 4, 1989

Related U.S. Application Data

[63] Continuation of Ser. No. 95,461, Sep. 11, 1987, abandoned, which is a continuation-in-part of Ser. No. 5,785, Jan. 22, 1987, Pat. No. 4,743,256, which is a continuation of Ser. No. 784,112, Oct. 4, 1985, abandoned.

[51] Int. Cl.$^4$ ............................. A61F 2/44; A61F 5/04
[52] U.S. Cl. ......................................... 623/17; 623/16; 606/61; 606/53; 606/76
[58] Field of Search ....................... 623/17, 18, 21, 22; 128/92 R, 924 M, 924 J, 924 F

[56] References Cited

U.S. PATENT DOCUMENTS

| | | | |
|---|---|---|---|
| 2,677,369 | 5/1954 | Knowles | 128/92 |
| 3,426,364 | 2/1969 | Lumb | 5/104 |
| 3,840,904 | 10/1974 | Tronzo | 623/22 |
| 3,848,601 | 11/1974 | Ma et al. | 128/305 |
| 3,855,638 | 12/1974 | Pilliar | 128/334 R |
| 3,867,728 | 2/1975 | Stubstad et al. | 128/DIG. 21 |
| 3,871,031 | 3/1975 | Boutin | 623/22 |
| 3,871,031 | 3/1975 | Boutin | 623/22 |
| 4,013,071 | 3/1977 | Rosenberg | 128/92 R |
| 4,164,794 | 8/1979 | Spector et al. | 623/22 |
| 4,206,516 | 6/1980 | Pilliar | 3/1.9 |
| 4,309,777 | 1/1982 | Patil | 623/17 |
| 4,349,921 | 9/1982 | Kuntz | 623/17 |
| 4,450,592 | 5/1984 | Niederer et al. | 623/22 |
| 4,501,269 | 2/1985 | Bagby | 128/92 |
| 4,550,448 | 11/1985 | Kenna | 623/16 |
| 4,553,273 | 11/1985 | Wu | 623/18 |
| 4,599,086 | 7/1986 | Doty | 623/17 |
| 4,662,891 | 5/1987 | Noiles | 623/22 |
| 4,714,469 | 12/1987 | Kenna | 623/17 |
| 4,725,280 | 2/1988 | Laure | 623/21 |
| 4,759,768 | 7/1988 | Hermann et al. | 623/21 |

FOREIGN PATENT DOCUMENTS

0042271A1  6/1981  European Pat. Off. .
DE
3505567A1  2/1985  Fed. Rep. of Germany .

OTHER PUBLICATIONS

PoroCoat—A Technical Review of Porous-Coated Implants for Biological Fixation—DePuy.
Article—"Anterior Discectomy and Interbody Fusion for Lumbar Disc Herniation"—Inoue, M.D. et al., No. 183, Mar. 1984.
Article—"Clinical Orthopaedics and Related Research-"—No. 193, Mar. 1985.

*Primary Examiner*—Alan W. Cannon
*Attorney, Agent, or Firm*—Hill, Van Santen, Steadman & Simpson

[57] ABSTRACT

Prosthesis plug implants forming transverse struts between adjacent vertebrae have roughened surfaces receiving bone ingrowth to fuse the plugs on prepared surface sites on opposed faces of adjacent vertebrae and have end faces with tool receiving recesses securing the plug on a tool for insertion on the prepared sites of the vertebrae and for removing the tool from the plug without disturbing its position on the sites. These sites are prepared by feeding a drill through a guide fixed to posterior or anterior sides of adjacent vertebrae to form transverse side-by-side channels including cortex bone in the opposed faces of the adjacent vertebrae and terminating the drilling in advance of the opposite sides of the vertebrae. A plurality of the plug implants are each threaded on the end of the tool surrounded by a sleeve and are inserted endwise in exact position on the prepared side-by-side sites. The sleeve is then pushed into a recess in the end of the plug and firmly held while the tool is unthreaded from the plug to prevent disturbing the exact position of the plug on the prepared sites.

9 Claims, 2 Drawing Sheets

U.S. Patent  Nov. 7, 1989  Sheet 1 of 2  4,878,915
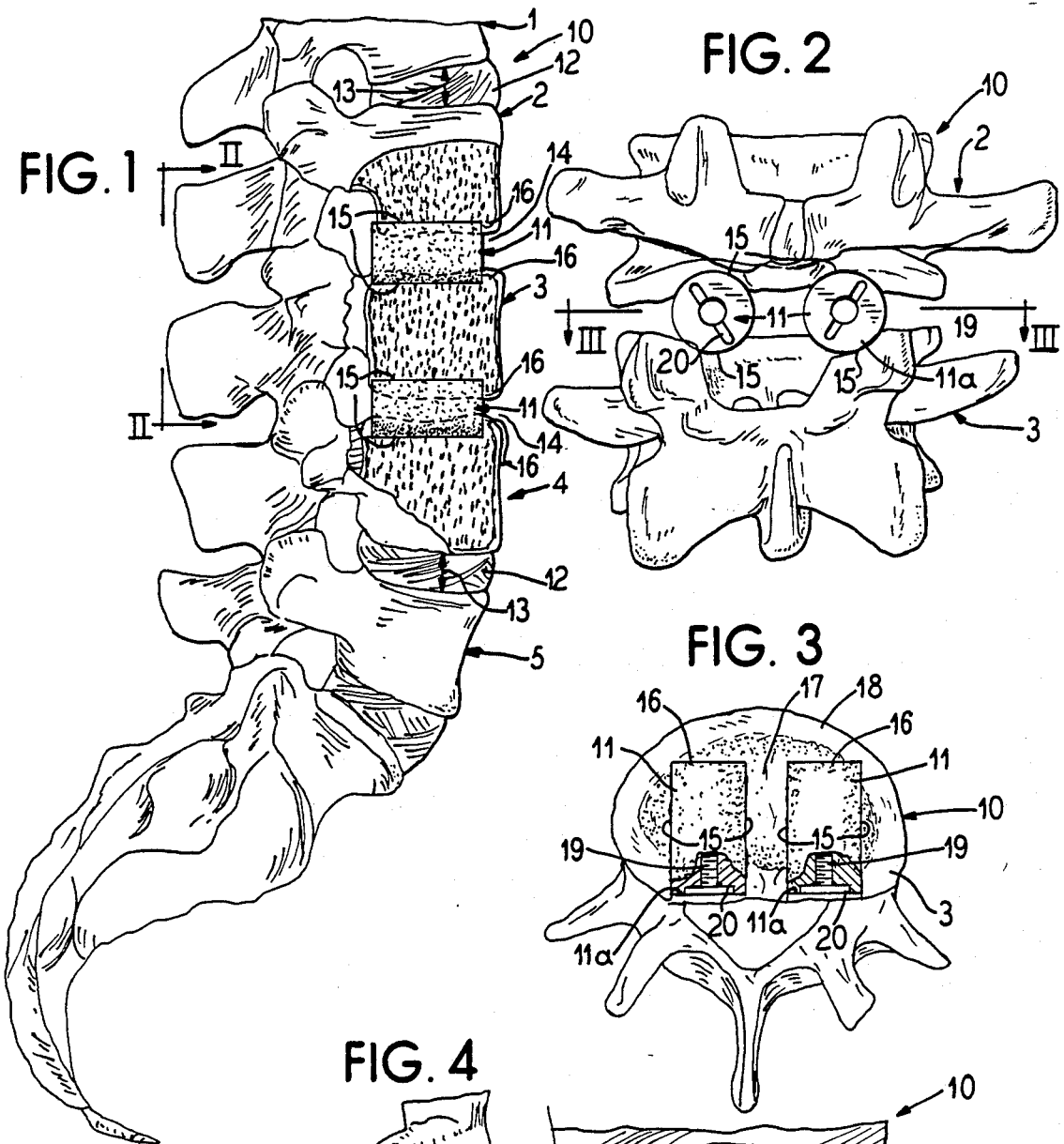
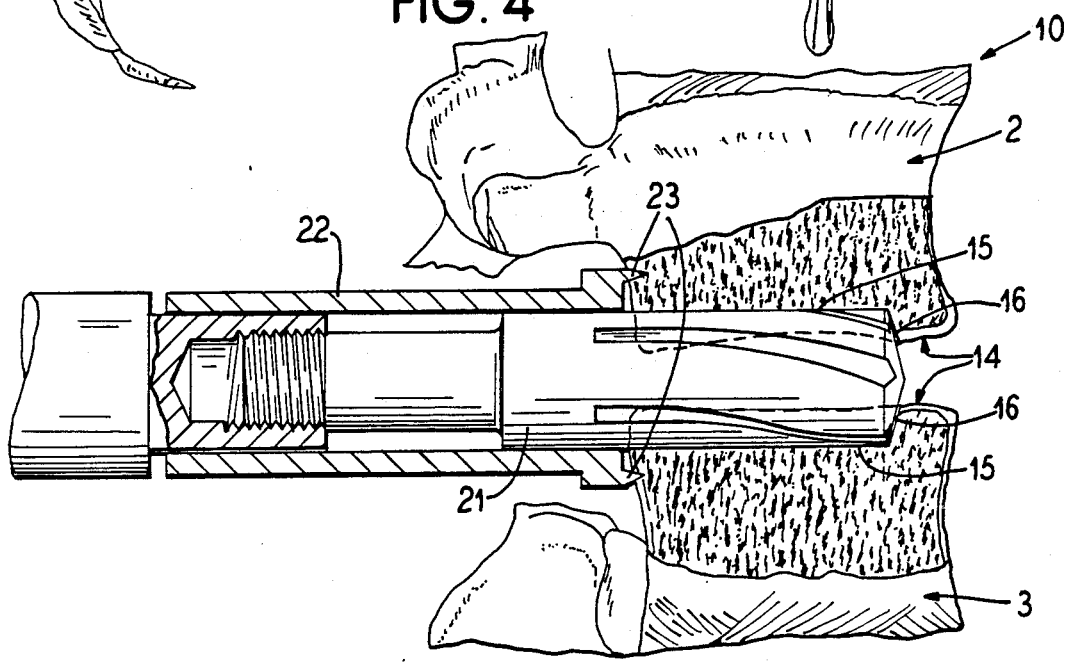

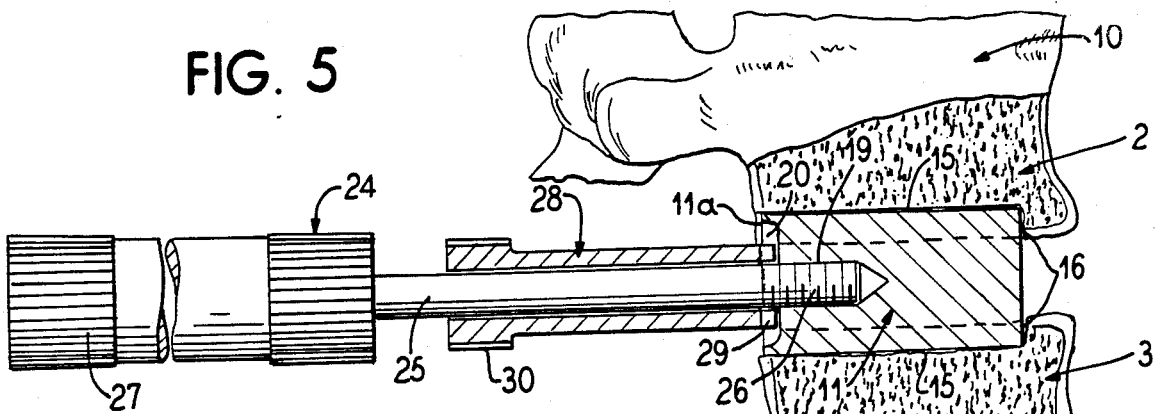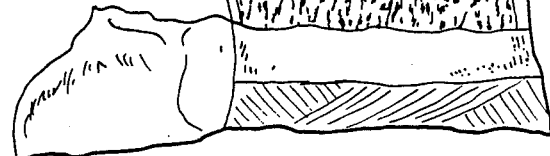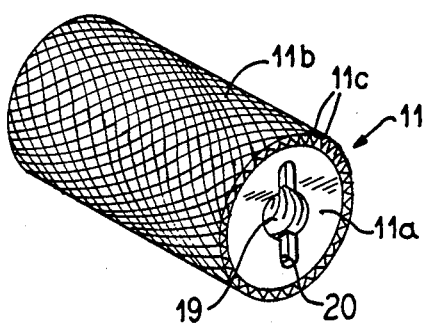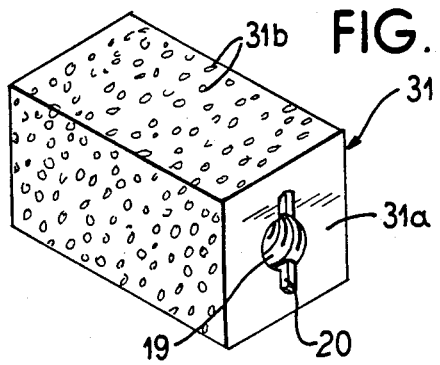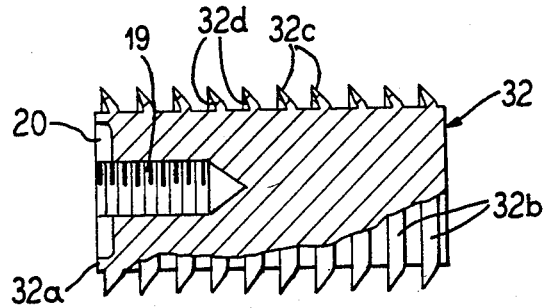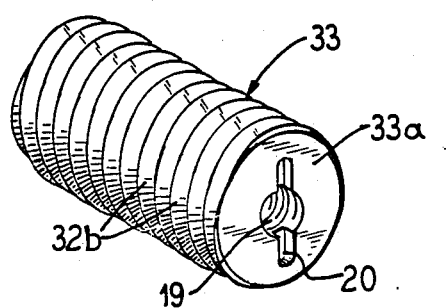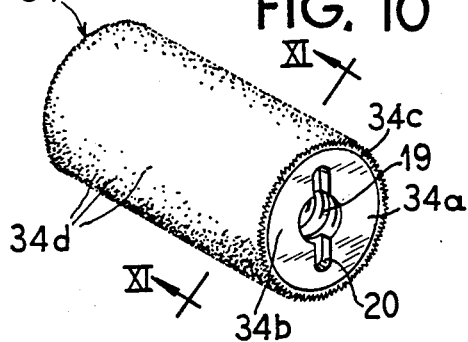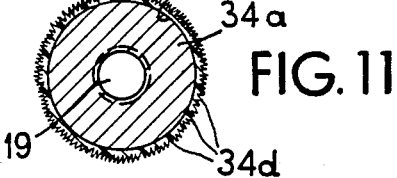

SURGICAL PROSTHETIC IMPLANT FACILITATING VERTEBRAL INTERBODY FUSION

RELATED APPLICATION

This is a continuation of application Ser. No. 095,461, filed Sept. 11, 1987, now abandoned, which is a continuation-in-part of 005,785, filed Jan. 22, 1987, now U.S. Pat. No. 4,743,256, which is a continuation of 784,112, filed Oct. 4, 1985, now abandoned.

BACKGROUND OF THE INVENTION

1. Field of the Invention

This invention relates to the art of prosthetic devices, methods and apparatus for implanting the devices between adjacent vertebrae to treat or prevent back pain in patients with ruptured or degenerated intervertebral discs. Specifically this invention deals with improvements in prosthetic strut forming plugs or blocks with roughened surfaces facilitating bone ingrowth from adjoining vertebrae.

2. Description of the Prior Art

As pointed out in my aforesaid Pat. No. 4,743,256 the leading cause of low back pain arises from rupture or degeneration of lumbar intervertebral discs. Pain in the lower extremeties of the back (sciatica) is caused by the compression of spinal nerve roots by damaged discs between the vertebra and low back pain is caused by collapse of the disc and the adverse effects of bearing the majority of the body weight through a damaged unstable vertebral joint. Surgical treatments for relief of the sciatic pain and lower back pain generally include the following:

1. Excision Of The Ruptured Soft Disc

This procedure removes the portion of the disc compressing the spinal nerve and is generally successful in relieving the sciatic leg pain but in more than half of the cases, there is a recurrence of back pain. Over a period of time the disc gradually loses height due to the rupture and this loss of height causes the posterior facet joints of the vertebrae to fit incorrectly resulting in arthritic change in all elements of the spinal segment. Recurrent nerve root compression due to bony encroachment (spinal stenosis) also develops. The continuing and recurring back pain from this source has created a leading source of pain and disability.

2. Disc Excision With Posterior Fusion

Traditional posterior fusion, creating bone growth between the bony laminae, or postero-lateral fusion between the transverse processes prevents motion between the adjacent vertebrae but does not alter the fact that approximately 90% of the body weight must be transmitted through degenerated discs causing pain. Further, posterior fusion tends to cause bony overgrowth leading to nerve root compression by spinal stenosis.

3. Disc Excision With Anterior Interbody Fusion

Interbody fusion techniques, in which the soft disc is completely excised and replaced with either the patient's own bone (autologous bone) or with transplant banked bone (homologous bone) are generally successful if solid fusion can be obtained between adjacent vertebrae bodies. Unfortunately, the success rate has only been about 50%.

4. Disc Excision With Posterior Lumbar Intervertebral Fusion (PLIF)

This procedure reconstructs the normal anatomic relationships between the bony and the neural structures and has many advantages. Weight bearing through a solid bony fusion mass between vertebral bodies relieves the mechanical pain of the traditional unstable degenerative disc and generally prevents long term disc collapse of further degenerative changes. The complete disc excision prevents recurrent herniation of the same degenerated disc.

However, this PLIF procedure has several serious disadvantages in that it is technically very difficult, and, therefore, not as successful or widely used as it might be. It entails large amounts of blood loss in a small deep hole causing physiological stress to the patient and psychological distress to the surgeon. Further, the use of autologous bone graft from the patient's own iliac crests extends the operation and creates a second painful operative site. Because it is difficult to obtain a large enough quantity of autogenous bone with sufficient strength, homologous bank bone is generally used.

Interbody bone grafting involves the problems of strength and that of bone incorporation. Strong cortex bone (the outer layer) is required as a strut in the interbody position to prevent collapse of the disc space while healing occurs. The surgeon has the unfortunate requirement of having to fashion the required struts with handheld tools during the operation and these cortex bone struts are not wide enough for optimum load bearing and they anchor themselves by healing process that occurs very slowly over a matter of years. Further, soft cancellous bone, which heals more reliably over a matter of 12 to 18 months, is also required for a traditional interbody fusion.

It is well understood in orthopaedic surgery, that grafted bone heals by a process called "creeping substitution" in which blood capillaries first grow into the grafted bone, the grafted bone is reabsorbed, and then new bone cells are laid down along the bony matrix of the graft. During the time that the structural bone grafts struts are being reabsorbed, motion must still be prevented in the involved segments and although a brace or cast is often used, the entire process has proven less reliable than desired. Homologous bank bone, being more "foreign", requires a much longer time to grow together and has a higher failure rate estimated at three times the failure as with the patient's own bone. In effect, neither source of bone is optimum for the fusion procedure.

My prior aforesaid Pat. No. 4,743,256 discloses an improved surgical procedure for eliminating spinal back pain caused by ruptured or degenerated vertebral discs by spanning the disc space between adjacent vertebrae with rigid implants having surfaces facilitating bone ingrowth and bottomed on prepared sites of the vertebrae to integrate the implant with the vertebrae and to provide a permanent weight supporting strut maintaining the disc space.

The present invention now further improves the art by providing the rigid implants with tool receiving end faces facilitating their insertion onto the prepared sites and having geometric patterns of roughened surfaces on the peripheries of the implants enhancing bone ingrowth. This invention also still further improves the art by refining the implant method with novel tools.

SUMMARY OF THE INVENTION

According to the invention rigid plugs of the type disclosed in my aforesaid U.S. Pat. No. 4,743,256 issued May 10, 1988 are further improved by providing end faces thereon with tool receiving recesses facilitating insertion of the plugs into place on the prepared sites of adjacent vertebrae and having roughened peripheral surfaces with patterns facilitating placement between the vertebrae and enhancing bone ingrowth. The preferred plugs have one end thereof provded with an internally threaded axial hole and wings or slots radiating from this hole in the end face. An insertion tool is threaded into the hole and is surrounded by a sleeve fitted into the slot recess. The plug, supported endwise on the tool is inserted in prepared sites of the adjacent vertebrae and when properly positioned, the sleeve is held against rotation and the tool unthreaded from the plug without shifting the plug.

The sites are preferably formed by a drill surrounded by a drill guard with projecting teeth embedded in the posterior ends of adjacent vertebrae to correctly position the drill for forming channels in the opposed faces of adjacent vertebrae. The channels are sufficiently wide and long to include hard cortex bone but preferably do not extend completely through the anterior side of the vertebrae. Conversely, if the drill is inserted from the anterior site of the vertebrae, the drilling operation is stopped short of the posterior side.

As disclosed in my aforesaid Pat. No. 4,743,256, the plugs are made of an inert rigid metal, such as stainless steel, cobalt-chromium-molybdenum alloys, titanium or the like. According to this invention, however, the peripheral surface of these plugs need not have a porous coating of metal particles, such as disclosed in my prior application, but can be provided with roughened surfaces forming pits, prongs, bristles, or the like irregularities for anchoring bone ingrowth. These roughened surfaces can be part of the plug body or a coating on the body, such as a resin polymer. Bristle or prong surfaces can be rigid or flexible and, if desired, shaped to facilitate insertion and resist retraction.

A preferred threaded hole in the end face of the plug terminates less than one half the length of the plug and has a diameter of less than ⅓ the diameter of the plug. The wing or slot radiates diametrically from the hole in the end face of the plug, but terminates inwardly from the periphery of the plug.

A preferred polymer coating to form the roughened surface is nylon, a poly-olefin, a vinyl, or the like resin resistent to deterioration in the environment of the implant.

It is then an object of this invention to improve the prosthetic devices of the type disclosed in my aforesaid Pat. No. 4,743,256 with an end face having a tool receiving configuration facilitating insertion of the devices in prepared sites of adjacent vertebrae.

Another object of this invention is to provide prosthetic implants of the type disclosed and claimed in my aforesaid Pat. No. 4,743,256 with roughened surfaces enhancing bone ingrowth to lock the implants with the vertebrae.

A still further object of this invention is to provide prosthetic plug implants used in side-by-side relation to form rigid transverse struts between adjacent vertebrae which are secured on the end of an insertion tool and removed from the tool without disturbing its inserted position.

A still further object of the invention is to provide a prosthetic implant plug to form a strut locking adjacent vertebrae in fixed relation while maintaining the disc space therebetween which has a roughened peripheral surface which deflects to facilitate insertion in prepared sites of adjacent vertebrae and locks in position on the sites.

Other and further objects and advantages of this invention will become apparent to those skilled in this art from the following detailed description of the drawings showing several preferred embodiments of the invention and in which:

FIG. 1 is a side elevational view of the lower portion of a human vertebral column with parts broken away and shown in section to illustrate prosthetic implants of this invention inserted between several of the lower vertebrae.

FIG. 2 is a posterior elevational view of a portion of FIG. 1 taken along the line II—II of FIG. 1.

FIG. 3 is a cross-sectional view with parts in elevation and broken away in section along the line III—III of FIG. 2.

FIG. 4 is an enlarged fragmentary side elevational view with parts shown in vertical section illustrating the manner in which the implant receiving sites of adjacent vertebrae are prepared.

FIG. 5 is a view similar to FIG. 4 illustrating the manner in which an implant is inserted in position on prepared sites of adjacent vertebrae.

FIG. 6 is a perspective view of one form of a prosthetic plug of this invention having a knurled periphery and showing the tool receiving recesses in an end thereof.

FIG. 7 is a perspective view of another form of implant plug of this invention having a pitted periphery.

FIG. 8 is a side elevational view with parts broken away and showing an axial section of a prosthetic plug of this invention with deflectable locking prongs on the periphery thereof.

FIG. 9 is a perspective view similar to FIG. 6 illustrating a threaded periphery on the plug providing roughened surfaces.

FIG. 10 is a perspective view of a prosthetic plug of this invention with a resin coating thereof having radiating bristles.

FIG. 11 is a transverse sectional view along the line XI—XI of FIG. 10.

AS SHOWN ON THE DRAWINGS

In FIGS. 1–5 the reference numeral 10 illustrates generally the lower portion of a human vertebral column with adjacent vertebrae supported on prosthetic implants of this invention or illustrating the manner in which sites are prepared for the implant and the manner in which an implant is inserted on the prepared sites.

In FIG. 1, the vertebral column 10 shows the five lower vertebrae numbered 1–5. Adjacent vertebrae Nos. 2 and 3 and adjacent vertebrae Nos. 3 and 4 are separated by and supported on prosthetic implants 11 of this invention. Vertebrae Nos. 1 and 2 and vertebrae Nos. 4 and 5 are illustrated as supported on and separated by healthy or undamaged human discs 12 maintaining a disc space 13 between the adjoining vertebrae.

The natural human discs have been excised from between discs Nos. 2 and 3 and Nos. 3 and 4 with the vertebrae spaces 14 being maintained by the implants 11. The opposed faces of adjoining discs have prepared sites or channels 15 formed therein generally transversely of the axis of the column 10 to snugly receive cylindrical opposite faces of the implants 11. These transverse sites 15 are sufficiently wide and deep to span the central soft cancellous bone and include the hard cortex bone of the adjacent vertebrae. However, the sites have blind ends 16 to bottom the implants 11.

As shown in FIGS. 2 and 3, the implants 11 are in the form of a pair of side-by-side cylindrical plugs inserted endwise on the transverse sites 15 which are fragmental cylindrical to receive and mate with opposite faces of these plugs.

The soft cancellous bone of the vertebrae is illustrated at 17 in FIG. 3 and is surrounded by the hard cortex bone 18 of the vertebrae No. 3. The prepared sites 15 include portions of this hard cortex so that the implants 11 span the softer cancellous bone 17 and rest on the hard cortex bone 18.

The plugs 11 fit snugly in the prepared sites 15 and are bottomed on the blind ends 16 of these sites.

The plugs are rigid, preferably solid, and have roughened surfaces forming extensive anchor points or pores for bone ingrowth from the adjoining vertebrae. They may be made of an inert metal, such as stainless steel, cobalt-chromium-molybdenum alloys, titanium, and the like. They may have many different shapes and peripheral surface configurations. They have an end face with tool receiving recesses so as to be mounted on the tool for insertion on the prepared site and for removal of the tool without disturbing the mounting. These tool receiving recesses are illustrated in the form of an internally threaded circular hole 19 tapped into one end face 11a of the plug. A radial slot 20 diametrically intersecting the tapped hole 19 is also provided in the end face 11a thus forming wings radiating from the tapped hole 19. The hole 19 extends axially inward from the end face 11a for a relatively short distance sufficient to provide a number of thread turns to be firmly anchored on the threaded end of an insertion tool.

As shown in FIG. 4, the sites 15 of the adjoining vertebrae Nos. 2 and 3 are easily prepared by a rotary drill or burr 21 slidable through a drill guard 22 with teeth or prongs 23 penetrating and anchored in the posterior side of both vertebrae. The drill is advanced through the sleeve 22 through the posterior sides of the vertebrae, but the drilling operation stops short of the anterior sides of these vertebrae so as to provide the blind ends 16 on the prepared sites.

While the sites 15 are easily prepared with the drilling apparatus illustrated in FIG. 4 it should be understood that sites of different shapes can be prepared with a mortise cutter or chisel shaped to conform with the shape of the implant to be inserted.

As shown in FIG. 5 the implant 11 is easily inserted on the prepared sites 15 from the posterior side of the vertebrae Nos. 2 and 3 by means of a tool assembly 24 having a stem 25 with a threaded end 26 mating with the tapped hole 19 in the end face 11a of the implant 11 and mounted in an easily grasped handle 27 at the opposite end. A sleeve 28 is slidably mounted on the stem 25 and has diametrically opposite keys or lugs 25 on its forward end fitting the radial slot 20. A knurled head 30 is provided on the opposite end of the sleeve.

The tool 24 with the sleeve 28 retracted on the stem 25 is threaded to expose the threaded end 26 of the stem is threaded into the tapped hole 19 and bottomed on the blind end thereof. The plug 11 is thus firmly mounted on the tool and the tool is manipulated to seat the plug on the prepared sites to be bottomed on the blind ends 16 of the sites 15. After positioning of the plug on the sites, the sleeve 28 is advanced on the stem 25 to bottom the prongs 29 in the slot 20 and the stem is unthreaded with the knurled head 30 of the sleeve being firmly held to prevent rotation of the sleeve and plug.

The plug 11 is illustrated in detail in FIG. 6 as having a solid cylindrical rod configuration with its circular end face 11a having the internally threaded hole 19 extending axially inward therefrom and with the diametric intersecting radial slot 20 providing the wings for receiving the prongs 29 of the sleeve 28. The cylindrical rod 11 has a knurled roughened peripheral surface 11b forming pyramid-like pits 11c for facilitating bone ingrowth. The plug is dimensioned to snugly fit on the prepared sites between the posterior and anterior side of the vertebrae. Its dimensions may vary widely to suit conditions and plug sizes of about ⅝" in diameter and about 1" in length are useful. The tapped hole 19 in the end face 11a of such a plug need only be about ¼" in diameter and ¼" in depth. The slot should terminate short of the periphery and need only be about ⅛" deep.

Another suitable form of prosthetic implant of this invention is illustrated in FIG. 7 where the device 31 has a square rectangular shape with an end face 31a having the tapped hole 19 and groove or slot 20. The device 31 has a pitted periphery 31b forming a myriad of small pores to facilitate bone ingrowth.

Another form of prosthetic device 32 is illustrated in FIG. 8 in the form of a cylindrical plug 32 with an end face 32a containing the tapped hole 19 and slot 20. The periphery of the cylindrical plug has longitudinally spaced circular ribs 32b. These ribs form dish-like prongs or barbs tilted toward the threaded end of the plug so that they will deflect to slide into the prepared sites but will bite into the bone to resist retraction from the sites. As illustrated the ribs have convex leading faces 32c and concave trailing faces 32d. Such configuration assists deflection when the plug is pushed into position but will spring back to resist reverse retraction or rotation. If desired the ribs can be axially slotted to provide a myriad of barbs.

In the embodiment 33 of FIG. 9 the implant is in the form of a solid cylindrical rod with an end face 33a containing the tapped hole 19 and slot 20 and with the cylindrical periphery being externally threaded as illustrated at 33b. The thread will advance the plug into the prepared sites when the plug is rotated in a clockwise direction. The threads can have sharp edges to bite into the bone structure.

The implant plug 34 of FIGS. 10 and 11 has the same end face 34a as the other plugs with the tapped hole 19 and slot 20, however, it has a solid rigid circular rod core 34b with a polymeric resin cover 34c with the peripheral surface of the cover having upright projecting bristles 34d. These bristles form extended surfaces facilitating bone ingrowth.

Many other types of rough or irregular surfaces can be provided on the devices of this invention including porous metal coatings composed of metal balls and beads sintered on a rigid metal substrate as further dislosed in the aforesaid Pat. No. 4,743,256.

The prosthetic implants are shown on the drawings as mounted in side-by-side parallel relation forming a pair of struts which maintain the disc space being snugly seated on hard cortex bone to carry the load. These implants have surfaces facilitating rapid bone ingrowth which will fuse the implants to the adjacent vertebrae in a relatively short growth period. However, while the plugs are illustrated as used in pairs, it should be understood that plugs of various shapes could be used singly to perform their function.

From the above descriptions and illustrations in the drawings it should be understood by those skilled in this art, that this invention has greatly improved the state of the art in avoiding the deficiencies of prior known techniques as set forth in the introduction to the specification. Many changes in constructions and different embodiments and applications of the invention may suggest themselves without departing from the spirit and scope of this invention and the foregoing description of the specific embodiments should not be construed as imposing unnecessary limitations on the dependent claims.

I claim as my invention:

1. A prosthetic plug implant for forming a rigid transverse strut between opposed prepared posterior to anterior transversely extending laterally spaced channels in faces of adjacent vertebrae of a vertebral column to maintain the disc space therebetween which comprises at least a pair of laterally spaced side-by-side rigid inert plugs sized and shaped to fit the prepared channels in the faces of the vertebrae and having roughened surfaces on the periphery thereof, said roughened surfaces having irregularities to interlock with the bone of the prepared channels and recesses for receiving bone to facilitate bone ingrowth, and said plugs each having an end face with tool receiving and mounting means extending internally of the plug to secure each plug endwise on the end of a tool for inserting the plug endwise transversely of the axis of the vertebral column in the prepared channels and to accommodate removal of the tool from the plug after insertion.

2. In a vertebral column with adjoining vertebrae bodies having spaced opposed faces with a disc space therebetween, each body having peripheral hard cortex bone surrounding soft cancellous bone and said faces having opposed posterior to anterior transverse prepared channels including said cortex bone, the improvement of at least two laterally spaced side-by-side rigid inert prosthetic plugs transversely spanning the disc space in a posterior to anterior direction with opposite faces bottomed on the bone of the prepared channels and providing a rigid transverse strut maintaining the disc space, a roughened surface on each plug, said roughened surface having barbs for biting into the bone and recesses between the barbs for receiving bone ingrowth to fuse the vertebrae bodies together, each plug having an end face with tool receiving means extending internally of the plug for securing the plug endwise on a first tool to facilitate endwise insertion of the plug in the prepared channels, and said end face having a second tool receiving recess to prevent rotation of the plug during removal of the first tool from the means extending internally of the plug.

3. A prosthesis for a vertebral column having transverse posterior to anterior prepared channels on opposed faces of adjoining vertebrae and a disc space between the adjoining vertebrae which comprises posterior to anterior laterally spaced side-by-side rigid inert plugs sized and shaped to form transverse posterior to anterior struts bottomed on the prepared channels of the adjoining vertebrae and maintaining a desired disc space between said adjoining vertebrae, each plug having a roughened surface biting into and interlocking with the bone of said prepared channels and providing irregularities to facilitate bone ingrowth from the vertebrae, and each plug having an end face with tool receiving means extending internally of the plug for removeably mounting the plug endwise on a tool to facilitate endwise insertion of the plug on the prepared channels.

4. The implant of claim 1, wherein the plug has a rigid biologically inert body and the roughened surfaces are barbs radiating from the body of the plug and having leading faces sloping toward the tool receiving end of the plug to facilitate insertion and to bite into the bone of the prepared channels of the vertebrae and provide extended areas receiving bone ingrowth.

5. The implant of claim 1, wherein the roughened surfaces are selected from the group consisting of knurled surfaces, pitted surfaces, barbed surfaces, bristle surfaces, and threaded surfaces engaging the prepared channels.

6. The implant of claim 1, wherein the roughened surfaces are barbs radiating from the plug periphery and deformable in the direction of insertion of the plug to facilitate insertion on the prepared sites and biting into the prepared sites upon attempted retraction of the plug.

7. The implant of claim 1, wherein the plug is a solid rod having a diameter sufficiently large to engage the hard cortex bone of the vertebrae and a length sufficient to span the soft cancellous bone of the vertebrae without projecting beyond the cortex bone.

8. The implant of claim 1, wherein the roughened surfaces are on the periphery of a plastics material coating of the plug.

9. The implant of claim 3, including a radial slot in the end face radiating from the internally threaded hole.

* * * * *